United States Patent [19]

Fukuhara et al.

[11] Patent Number: 5,227,563
[45] Date of Patent: Jul. 13, 1993

[54] PREPARATION OF PROPYLENE BY DEHYDRATION OF ISOPROPANOL IN THE PRESENCE OF A PSEUDO-BOEHMITE DERIVED GAMMA ALUMINA CATALYST

[75] Inventors: Hiroshi Fukuhara, Ichihara; Fujihisa Matsunaga, Wakayama; Mitsuki Yasuhara, Yotsukaido; Shintaro Araki, Ichihara; Toshiyuki Isaka, Iwakuni, all of Japan

[73] Assignee: Mitsui Petrochemical Industries, Ltd., Tokyo, Japan

[21] Appl. No.: 700,319

[22] Filed: May 9, 1991

Related U.S. Application Data

[63] Continuation-in-part of Ser. No. 564,706, Aug. 9, 1990, abandoned, which is a continuation of Ser. No. 450,539, Dec. 14, 1989, abandoned.

[30] Foreign Application Priority Data

Dec. 26, 1988 [JP] Japan .................................. 63-328721
Oct. 13, 1989 [JP] Japan .................................. 1-267553

[51] Int. Cl.$^5$ ................................................. C07C 1/00
[52] U.S. Cl. ................................... 585/640; 585/639
[58] Field of Search ....................... 585/640, 324, 328

[56] References Cited

U.S. PATENT DOCUMENTS

| | | | |
|---|---|---|---|
| 1,895,529 | 1/1933 | Taylor et al. | 585/640 |
| 2,636,057 | 4/1953 | Cutcher et al. | 585/640 |
| 4,514,511 | 4/1985 | Jacques et al. | 502/355 |
| 4,602,119 | 7/1986 | Drake | 502/355 |
| 4,708,945 | 11/1987 | Murrell et al. | 502/355 |

FOREIGN PATENT DOCUMENTS

| | | |
|---|---|---|
| 1065408 | 9/1959 | Fed. Rep. of Germany ...... 585/640 |
| 59-19927 | 5/1984 | Japan . |
| 59-118895 | 1/1986 | Japan . |
| 61-23771 | 6/1986 | Japan . |
| 64-34929 | 2/1989 | Japan . |

OTHER PUBLICATIONS

European Search Report for Application No. EP 89 31 3328, May 4, 1990.

*Primary Examiner*—Theodore Morris
*Assistant Examiner*—Walter D. Griffin
*Attorney, Agent, or Firm*—Nixon & Vanderhye

[57] ABSTRACT

Propylene can be prepared in high yield and selectivity by dehydrating isopropanol in the presence of a γ-alumina catalyst having a mean pore diameter of from 30 to 150 Å with a standard deviation ($\sigma_n$) of from 10 to 40 Å based on statistic calculation from pore diameter and pore volume.

6 Claims, 2 Drawing Sheets

PREPARATION OF PROPYLENE BY DEHYDRATION OF ISOPROPANOL IN THE PRESENCE OF A PSEUDO-BOEHMITE DERIVED GAMMA ALUMINA CATALYST

This is a continuation-in-part of application Ser. No. 07/564,706, filed Aug. 9, 1990, now abandoned, which is a continuation of Ser. No. 07/450,539, filed Dec. 14, 1989, now abandoned.

This invention relates to the preparation of propylene, and more particularly, to the preparation of propylene from isopropanol in high yield and selectivity.

BACKGROUND OF THE INVENTION

It is prevalent in the prior art to prepare isopropanol from propylene, but it has never been a practice to prepare propylene from isopropanol. Nevertheless, the current situation where acetone is by-produced in surplus in the phenol preparation by the cumene process imposes it under consideration to prepare propylene from isopropanol resulting from hydrogenation of acetone. More particularly, the mainstream of the current industrial phenol preparation is the cumene process. The phenol preparation by the cumene process involves forming cumene from benzene and propylene, automatically oxidizing the cumene into cumene hydroperoxide, and subjecting the cumene hydroperoxide to decomposition in the presence of an acid catalyst to form phenol and acetone. The phenol preparation by the cumene process is a cost efficient method insofar as the demands for phenol and acetone keep balance.

The demand for acetone is decreasing in the recent years. Although the use of acetone as a starting material toward methyl methacrylate was a major demand for acetone, the methyl methacrylate preparation was switched to the use of compounds having 4 carbon atoms. As a consequence, there is a decreasing demand for acetone.

It is thus desired to make efficient use of acetone without leaving acetone as a by-product. One promising attempt is to convert acetone into isopropanol and dehydrating isopropanol back to propylene. It is now required to develop a process for preparing propylene from isopropanol which has never been sought in the previous circumstances.

Among classical methods for the preparation of olefins, it is well known to subject alcohols to dehydration in the presence of strong acids such as sulfuric acid, phosphoric acid, perchloric acid, phosphotungstic acid, and phosphomolybdic acid. Although the preparation of olefins is predominantly based on naphtha cracking in recent years, a variety of proposals have been made on alcohol dehydration to prepare olefins for the purposes of rendering diverse reactants available for olefin preparation and producing olefins of high purity. For example, it was proposed to produce ethylene by dehydrating ethanol as disclosed in Japanese Patent Publication Nos. 40057/1984 and 19927/1984 and to produce high purity isobutylene by dehydrating tertiary butanol as disclosed in Japanese Patent Publication No. 23771/1986 and Japanese Patent Application Kokai No. 26/1986. As to the catalyst for assisting in preparation of ethylene through dehydration of ethanol, it is proposed to use solid acid catalysts such as alumina, silica, silicaalumina, zeolites and solid phosphoric acids as disclosed in Japanese Patent Application Kokai No. 34929/1989.

As for the conversion of isopropanol to propylene through dehydration, however, no appropriate process is available other than the above-mentioned strong acid catalyzed dehydration. Although it might occur to those skilled in the art to apply the conventional technique for dehydrating ethanol or tertiary butanol, no presumption can be made because the end products, ethylene or isobutylene and propylene are considerably different in nature.

In general, the use of strong acid catalysts has problems that the reactor used must be of expensive corrosion-resistant material and the outgoing used acid must be disposed of with difficulty. In addition, the once produced olefins can react in the presence of strong acids, for example, they can polymerize into higher molecular weight polymers or isomerize into undesired compounds, resulting in reduced yields of the end olefins. Further, propylene is more active than ethylene and isobutylene and susceptible to polymerization. This suggests that it is impossible to apply the methods described in Japanese Patent Publication Nos. 40057/1984, 19927/1984, 23771/1986, and 26/1986 to the preparation of propylene.

On the contrary, the method for the preparation of ethylene through dehydration of ethanol in the presence of solid acid catalysts described in Japanese Patent Application Kokai No. 34929/1989 is advantageous in that a simple reactor of less expensive material may be used because the catalysts are not corrosive. However, silica-alumina, zeolites, and solid phosphoric acids are strongly acidic. If isopropanol in gas state is passed through a reactor charged with such a strongly acidic catalyst at relatively low temperatures of 250° to 300° C., as much as about 30% of the resulting propylene is further catalyzed into polymers. Formation of substantial amounts of high molecular weight polymeric by-products results in reduced yields of propylene. Dehydration of isopropanol into propylene is a substantial endothermic reaction requiring a reaction temperature of at least 250° C., at which the above-mentioned strong acid catalysts are unfeasible as industrial catalysts.

The alumina catalysts are known to be effective for dehydration of ethanol. However, if commercially available alumina catalysts are applied to dehydration of isopropanol, propylene would not be obtained in high yields. It would be possible to increase the percent conversion of isopropanol by raising the reaction temperature to 450° C. or higher. However, propylene is obtained in low yields since cracking reaction occurs simultaneous with dehydration at elevated temperatures so that the resulting propylene contains substantial amounts of impurities.

SUMMARY OF THE INVENTION

Figure 1:
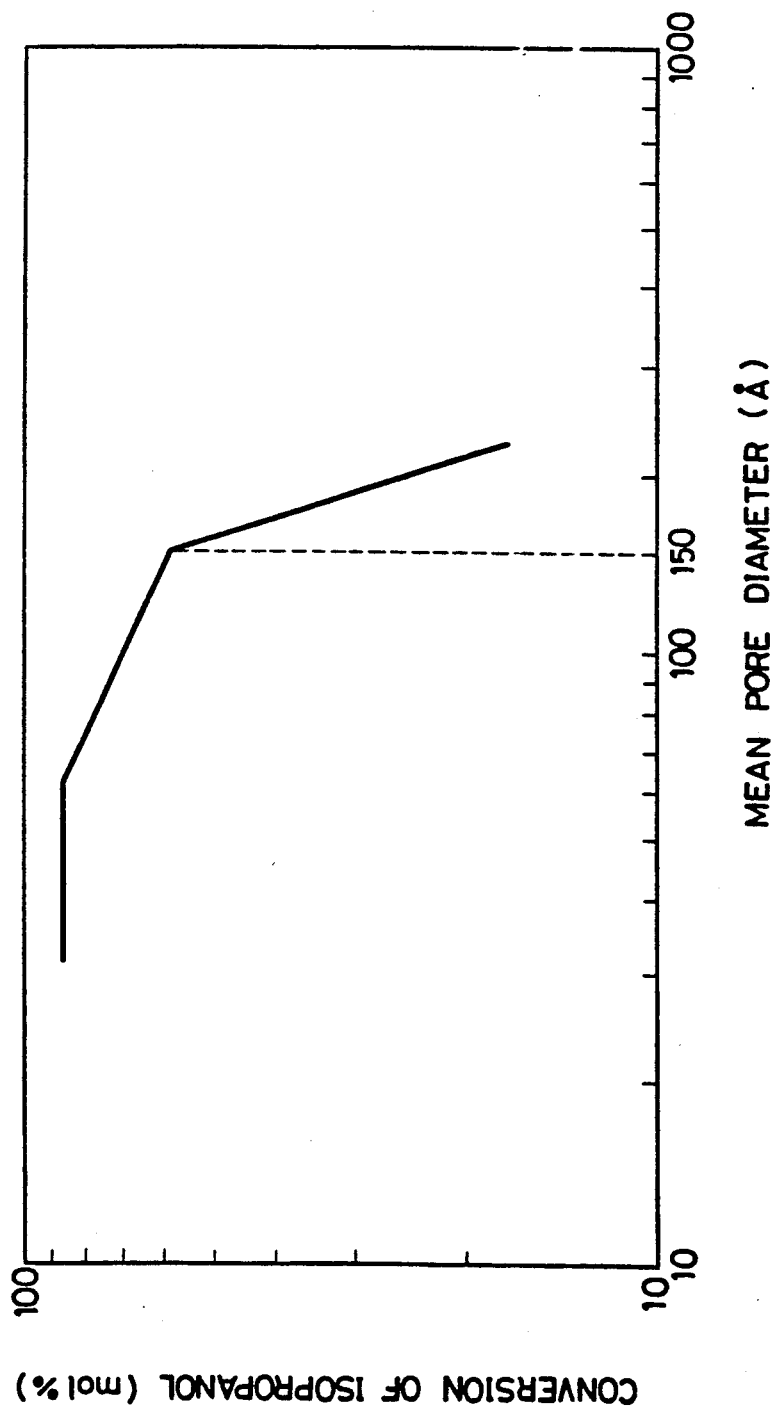
FIG. 1 is a diagram showing the conversion of isopropanol as a function of the mean pore diameter of catalyst.

Therefore, a primary object of the present invention is to provide a process for preparing propylene from isopropanol in high yield and selectivity using a simple reactor at lower temperatures than required in the conventional processes. A reactor of expensive corrosion-resistant material need be used no longer.

The present invention provides a process for preparing propylene comprising the step of dehydrating isopropanol in the presence of a catalyst. According to the feature of the invention, the catalyst is of gamma-alumina having a mean pore diameter in the range of from 30 to 150 Å with a standard deviation ($\sigma_n$) in the range of from 10 to 40 Å based on statistic calculation from pore diameter and pore volume.

Preferably, isopropanol in gas state is passed through a catalyst layer of the $\gamma$-alumina in a direction so as to satisfy the following equation:

$$(M \times R \times T)/(3.6 \times P \times \pi \times r^2) \geq 1 \quad (I)$$

wherein

M is moles of isopropanol fed per hour, mol/hr,
R is the gas constant equal to 0.082 l·atm/deg·mol,
T is a temperature of the catalyst layer in °K.,
P is a reaction pressure in atm,
$\pi$ is the circle ratio equal to 3.14, and
r is a radius of the catalyst layer in a cross section transverse to the direction of flow of isopropanol in cm.

DETAILED DESCRIPTION OF THE INVENTION

Isopropanol used as the starting reactant in the process of the present invention may be obtained by any well-known methods. The method for preparing isopropanol is not critical. Industrial benefits are great when use is made of the isopropanol which is obtained through suitable techniques from the acetone which is a by-product in preparing phenol by the cumene process.

The catalyst used in preparing propylene by dehydrating isopropanol according to the invention is a porous $\gamma$-alumina having a specific pore distribution, that is, having a mean pore diameter in the range of from 30 to 150 Å, preferably from 40 to 70 Å with a standard deviation ($\sigma_n$) in the range of from 10 to 40 Å, preferably 10 to 20 Å based on statistic calculation from pore diameter and pore volume.

The pore distribution used herein is a distribution representative of the relationship between a pore diameter (2r') and a corresponding pore volume, that is, a proportion of an infinitesimal change of pore volume (dPV) relative to an infinitesimal change of pore radius (dr'), dPV/dr', which can be determined by an analysis of isothermal adsorption/desorption curves of nitrogen gas at the temperature of liquid nitrogen by Cranston-Inkey method. The pore distribution used herein also implies the diameter (mean pore diameter) across which pores are centrally distributed on average as well as the width of distribution of the pore diameter. The mean pore diameter and the standard deviation ($\sigma_n$) which means the width of distribution of the pore diameter are herein considered to be equivalent to the pore distribution, provided that the pore distribution is a statistic distribution.

The $\gamma$-alumina catalyst is prepared from pseudo-boehmite aluminum hydroxide through dehydration. The catalyst so prepared from pseudo-boehmite aluminum hydroxide has a filament type crystal structure which together with the other catalyst characteristics specified herein is uniquely suited to the conversion of isopropanol to propylene by dehydration. Other sources or types of aluminum hydroxide when dehydrated to an alumina catalyst do not achieve such high isopropanol conversions.

The $\gamma$-alumina catalyst having a specific pore distribution within the above-define range is effectively in producing propylene at high purity in high yields from isopropanol.

The $\gamma$-alumina having the above-defined nature used as the catalyst in the practice of the present invention should preferably have the following nature at the same time.

It is preferred that the $\gamma$-alumina catalyst has a total pore volume of at least 0.4 cc/g, more preferably 0.5 to 0.8 cc/g on dry basis.

Also preferably the $\gamma$-alumina is a low alkali $\gamma$-alumina comprising at least 90% by weight of $\gamma$-alumina, less than 10% by weight of silica, and up to 0.5% by weight of an alkali metal oxide, more preferably at least 95% by weight of $\gamma$-alumina, less than 5% by weight of silica, and up to 0.3% by weight of an alkali metal oxide.

Also preferably, the $\gamma$-alumina catalyst is a weakly acidic $\gamma$-alumina having a pKa value in the range of from +3.3 to +6.8 as measured with Hammett's indicator, and an integrated acid quantity of up to 0.5 meq/g, on dry basis.

The $\gamma$-alumina catalysts having a mean pore diameter within the above-defined range and an acidity represented by a pKa value within the above-defined range are effective in producing propylene of higher purity in high yields.

The reasons for such limitations of catalyst are obvious from the following experiments.

(1) Relationship between mean pore diameter and catalytic activity.

Dehydration of isopropanol was performed using a $\gamma$-alumina catalyst, with its mean pore diameter ranging from 31 to 190Å, under the following reaction conditions. The results are shown in Table A and FIG. 1.

TABLE A

| Reaction conditions | |
|---|---|
| isopropanol: | LHSV = 3.0 hr$^{-1}$ |
| pressure: | 18 kg/cm$^2$ G |
| catalyst layer temp.: | 300° C. |
| contact time: | about 35 seconds |
| Catalyst | |
| $\gamma$-alumina (Na$_2$O contents, 0.05 wt %) | |

| No. | Mean pore diameter (Å) | Conversion of isopropanol (mol %) |
|---|---|---|
| 1 | 31 | 86.8 |
| 2 | 40 | 87.1 |
| 3 | 62 | 86.8 |
| 4 | 75 | 74.9 |
| 5 | 114 | 68.9 |
| 6 | 150 | 59.1 |
| 7 | 160 | 52.2 |
| 8 | 190 | 27.1 |

Correlation between the conversion ratio of isopropanol and mean pore diameter is shown in FIG. 1 precisely by using a log-log graph paper.

Three steps of changes were found between the conversion ratio of isopropanol and mean pore diameter: the conversion ratio of isopropanol was constant while mean pore diameters were small, but, as the pore diameter became large and exceeded 70Å, the conversion ratio started to decrease gradually and then rapidly when the pore diameter exceeded 150 Å.

On the basis of the above reasons, mean pore diameter of the $\gamma$-alumina catalyst to be used is set up to 150Å or below. Also, mean pore diameter of the $\gamma$-alumina catalyst to be used is set up to 30Å or above, because preparation of γ-alumina with mean pore diameter being less than 30Å is quite difficult to be achieved by means of the current alumina preparation technique.

(2) Relationship between Na₂O contents and catalytic activity.

Dehydration of isopropanol was performed using γ-alumina catalysts having different Na2O contents as shown below, under the following reaction conditions. The results are shown in Table B and FIG. 2.

TABLE B

| Reaction conditions | |
|---|---|
| isopropanol: | LHSV = 3.0 hr⁻¹ |
| pressure: | one atmosphere |
| catalyst layer temp.: | 260° C. |
| contact time: | 2 seconds |
| Catalyst | |
| γ-alumina | |
| mean pore diameter: | 59Å |
| σn: | 13Å |
| total pore volume: | 0.56 cc/g (on dry basis) |
| specific surface area: | 267 m²/g (on dry basis) |

| No. | Na₂O contents (wt %) | Conversion of isopropanol (mol %) |
|---|---|---|
| 1 | 0.05 | 94.1 |
| 2 | 0.26 | 87.3 |
| 3 | 0.47 | 51.9 |
| 4 | 0.55 | 27.5 |
| 5 | 0.71 | 12.5 |

Figure 2:
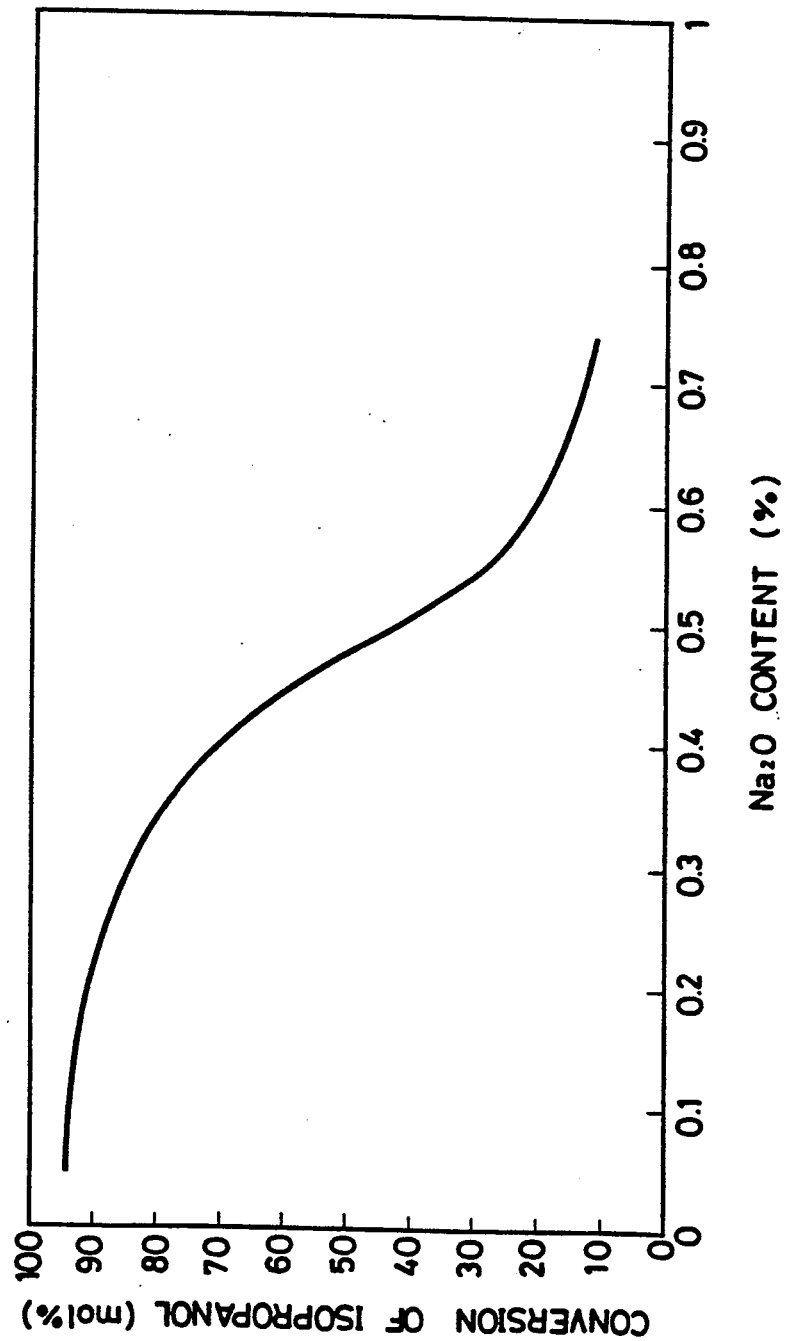
FIG. 2 is a diagram showing the conversion of isopropanol as a function of the $Na_2O$ content of catalyst.

As is evident from Table B and FIG. 2, the conversion ratio of isopropanol decreases rapidly when the Na₂O content of γ-alumina catalyst exceeds 0.5 wt%. On the basis of this reason, an alkali metal oxide content of γ-alumina was set up to 0.5 wt%.

The γ-alumina catalyst of the present invention characterized by a specific pore distribution, low alkali content, and weak acidity as defined above may be obtained by mixing sodium aluminate and aluminum sulfate, precipitating aluminum hydroxide from the mixture, and working up the precipitate by washing, aging, jet drying, granulating, drying and other suitable steps so as to control the pore distribution and other attributes to the desired ones.

The γ-aluminas used herein may be treated with acids and/or baked if desired. The acid treatment is carried out by immersing the γ-alumina in an acid for the purpose of adjusting the acidity of the catalyst. The acids used include aqueous solutions of hydrochloric acid, nitric acid, and boric acid as well as carboxylic acids such as acetic acid, formic acid, and oxalic acid. The baking may be carried out by heating the catalyst at a temperature of 400° to 700° C. in air or a reducing atmosphere.

The catalyst used herein may be in either powder or granular form. Spherical γ-alumina catalysts are preferred, especially in the form of spheres having a sphere size of up to 1/10, more preferably 1/10 to 1/1000 of the diameter of a cylindrical reactor which is loaded with a layer of the catalyst. Such spherical catalysts are effective in preventing divagation and back-mixing of reactant and product gases through the reactor, thereby maintaining the conversion of isopropanol high and the selectivity and yield of propylene high.

The catalyst used herein has a markedly extended lifetime. When an ordinary solid acid is used as the catalyst for dehydration of isopropanol, the reaction readily takes place if the acid has a high acidity, but with the disadvantage that undesirable polymerization of the resulting propylene is simultaneously induced such that the polymer is adsorbed to the catalyst which immediately lose its activity. However, the γ-alumina catalyst having physical properties within the above-defined ranges according to the present invention does not experience a loss of activity by the above-mentioned mechanism.

Further, the γ-alumina catalyst used herein can be regenerated even if its catalytic activity lowers. Regeneration may be carried out by burning off carbonaceous deposits in the presence of air, for example. The temperature at which used catalysts are heated for regeneration is preferably in the range of from about 300° to about 600° C., more preferably from 400° to 550° C.

In the practice of the invention, dehydration of isopropanol is preferably carried out in the following conditions. The reaction temperature is in the range of from about 150° to about 500° C., more preferably from 180° to 400° C. The reaction pressure may be reduced, atmospheric or increased pressure. It is preferred to keep the reaction system under gas phase conditions. The feed of isopropanol to the reactor is in the range of from 0.1 to 20 hr⁻¹, more preferably 0.5 to 10 hr⁻¹ in liquid hourly space velocity (LHSV).

In order that the propylene resulting from the reaction immediately exit the reaction system, a gaseous substance inert to dehydration may be introduced in admixture with the reactant. Such gas carriers include water, nitrogen, carbon dioxide, helium, argon, methane, ethane, propane, and butane, for example. The gaseous substances may encompass those substances which are liquid prior to entry to the reactor, but become gaseous under the reaction conditions. Examples of such gas-forming substances include aliphatic hydrocarbons such as pentane, hexane, heptane, cyclopentane, cyclohexane, and aromatic hydrocarbons such as benzene, toluene, xylene, ethylbenzene, and cumene.

The gaseous substance is admitted into the reactor along with isopropanol in such a proportion that about 0.05 to about 10 mol of the gaseous substance is present per mol of isopropanol. Excess use of the gaseous substance is not recommended for economy in that a large amount of inert gas should be separated from the reaction product which is a mixture of propylene and water and recycled to the reactor, requiring increased costs for separation and recycle.

The process of the invention favors continuous reaction while the reactor is preferably of a fluidized bed system loaded with a powder catalyst or a fixed bed system loaded with a granular catalyst.

In one preferred embodiment of the invention, propylene is produced by feeding isopropanol in gas state through a catalyst layer of the γ-alumina as defined above in a cylindrical reactor in an axial direction thereof so as to satisfy the following equation:

$$(M \times R \times T)/(3.6 \times P \times \pi \times r^2) \geq 1 \qquad (I)$$

wherein M is moles of isopropanol fed per hour, mol/hr; R is the gas constant equal to 0.082 l·atm/deg·mol; T is a temperature of the catalyst layer in °K.; P is a reaction pressure in atm; π is the circle ratio equal to 3.14; and r is a radius of the catalyst layer in a cross section transverse to the direction of flow of isopropanol in cm.

In this embodiment, the catalyst layer is preferably in the form of a cylindrical thin layer having the radius r and an axial thickness. The feed of isopropanol to the reactor (corresponding to M) is in the range of from 0.1 to 20 hr$^{-1}$, more preferably 0.5 to 10 hr$^{-1}$ in liquid hourly space velocity (LHSV). The reaction temperature T is usually in the range of from about 150° to about 500° C., preferably from 180° to 400° C. The reaction pressure P may be reduced, atmospheric or increased pressure although the reaction system should preferably be kept under gas phase conditions.

With a proper choice of M, T, P and r such that the value of reaction factor $(M \times R \times T)/(3.6 \times P \times \pi \times r^2)$ is at least 1, preferably in the range of from 1 to 10, propylene can be efficiently prepared by feeding isopropanol through a solid catalyst layer in the reactor where dehydration of isopropanol takes place. If isopropanol is fed under such conditions that the value of $(M \times R \times T)/3.6 \times P \times \pi \times r^2)$ is less than 1, then the rate of dehydration of isopropanol, that is, the percent conversion of isopropanol becomes low. Then in order to accomplish the desired reaction rate, the reaction temperature must be increased at the sacrifice of purity and yield. Elevated reaction temperatures not only increase formation of by-products resulting in reduced purity and yield of propylene, but would also reduce the catalyst life. Further, reaction factors outside the range allow reactant and product gases to be back mixed in the reactor to retard dehydration, tending to form more by-products.

The reactor is not critical to the invention and may be selected from those reactors commonly used in this type of reaction. For example, a tubular reactor may be used having a fixed bed of catalyst layer wherein the reactant gas is passed through the catalyst layer in an axial direction, and a fixed bed system reactor having a solid catalyst layer of spherical catalyst grains is preferred. The flow of the reactant gas may be vertically upward or downward although the down flow is preferred in preventing hopping of the catalyst grains.

Since dehydration of isopropanol is a substantial endothermic reaction, it is necessary to supply reaction heat in an efficient manner. For adiabatic fixed bed reactors, an intermediate heat-exchange multi-stage adiabatic reactor is preferred wherein the catalyst layer is divided into plural stages and heat exchangers (or heat sources) are provided between adjoining stages. Another useful reactor is a self heat-exchange type reactor wherein preheated isopropanol gas is conducted through a conduit extending through a catalyst layer for heat exchange with the catalyst layer to heat the catalyst layer.

Also useful is a multi-tube heat-exchange reactor wherein a plurality of thin reaction tubes are arranged in juxtaposition and a heating medium is passed outside the tubes. The heating medium used herein may be hot oil or molten salt (a mixture of NaNO$_3$ and KNO$_3$). Alternatively, a direct heating reactor may be used wherein a reaction tube is received in a reaction furnace such that the reaction tube is directly heated by means of gas burners.

In the practice of the invention, dehydration of isopropanol in the catalyst layer is believed to follow the process that gaseous molecules of isopropanol migrate from the mobile phase to the outer surface of solid catalyst grains of $\gamma$-alumina through external diffusion and then to the inner surface of catalyst grains through intra-pore diffusion. The gaseous molecules of isopropanol are then adsorbed to active sites on the catalyst where dehydration takes place. Propylene and water thus formed migrate through pores by reverse diffusion and leave the outer surface of catalyst grains to go back to the mobile phase. It is thus believed that dehydration of isopropanol largely depends on the external diffusion and intra-pore diffusion. Therefore, the rate of dehydration of isopropanol is significantly increased by using a $\gamma$-alumina catalyst having a specific pore size distribution closely related to the external diffusion and intra-pore diffusion of gaseous isopropanol molecules in the catalyst layer. The rate of dehydration is further promoted by feeding isopropanol through the solid catalyst layer so that the reaction factor $(M \times R \times T)/(3.6 \times P \times \pi \times r^2)$ is at least 1, that is, equation (I) is met, thereby increasing the diffusion rate.

The propylene preparing process of the invention is beneficial to the industry for efficient utilization of an acetone by-product under the current situation where the acetone by-product formed in preparing phenol by the cumene process finds a decreasing application. The present invention constitutes a part of the overall process involving first converting the acetone into isopropanol and then converting the isopropanol into propylene through dehydration so that as a whole, acetone is converted into propylene, that is a starting material for the synthesis of cumene. In addition to its use in the cumene process, propylene also finds a promising application as a starting material for the preparation of polyolefins.

EXAMPLE

Examples of the present invention are given below by way of illustration and not by way of limitation.

EXAMPLE 1

A vertical tubular reactor of stainless steel having an inner diameter of 25.4 mm (1 inch) and a length of 500 mm at approximately a central zone was loaded with 20 ml of $\gamma$-alumina having the following physical properties.

Gamma-alumina catalyst

Mean pore diameter: 69 Å
    standard deviation ($\sigma_n$) 13 Å
Total pore volume: 0.66 cc/g
Specific surface area: 275 m$^2$/g
Grain size: 8–14 mesh
Acidity distribution:
    pKa$\leq$6.8: 0.39 meq/g
    pKa$\leq$4.8: 0.08 meq/g
    pKa$\leq$3.3: 0
    pKa$\leq$1.5: 0
    pKa$\leq$−3.0: 0
Integrated acid quantity: 0.39 meq/g
Composition (dry basis):
    Na$_2$O: 0.2% by weight
    SiO$_2$: 0.06% by weight
    Fe$_2$O$_3$: 0.02% by weight
    $\gamma$-alumina: 99.75% by weight Isopropanol was fed into the reactor from its top at a flow rate of 60 ml/hr (LHSV 3 hr$^{-1}$) at a reaction temperature of 320° C. and a pressure of 10 kg-f/cm$^2$ G. The gas/liquid mixture from the reactor bottom was separated into a liquid reaction mixture and a gas product. When 8 hours had passed since the start of reaction, the liquid reaction mixture and the gas product were delivered in average hourly amounts of 14.4 g/hr. and 18.8 liter/hr. The liquid reaction mixture and the gas product were analyzed by gas chromatography for the evaluation of isopropanol dehydration, finding an isopropanol conversion rate of 98.4% and a propylene yield of 98.0%. The by-product was 0.4% of acetone. The gas product was propylene with a purity of 99.5%.

It is to be noted that the conversion of isopropanol and the selectivity and yield of propylene are calculated by the following equations.

$$\text{Percent conversion of isopropanol} = \frac{\text{moles of isopropanol reacted per unit time}}{\text{moles of isopropanol fed per unit time}} \times 100$$

$$\text{Percent selectivity of propylene} = \frac{\text{moles of propylene produced per unit time}}{\text{moles of isopropanol reacted per unit time}} \times 100$$

$$\text{Percent yield of propylene} = \frac{\text{moles of propylene produced per unit time}}{\text{moles of isopropanol fed per unit time}} \times 100$$

EXAMPLES 2-5

The procedure of Example 1 was repeated except that the amount of isopropanol fed and the reaction temperature were changed as reported in Table 1. The results are shown in Table 1 together with the results of Example 1.

TABLE 1

| | Dehydration of isopropanol | | | | |
|---|---|---|---|---|---|
| | Isopropanol | | Reaction | | |
| Example No. | Flow rate (ml/hr) | LHSV (/hr) | temp. (°C.) | Isopropanol conversion (%) | Propylene yield (%) | Amount (%) of by-products* |
| 1 | 60 | 3 | 320 | 98.4 | 98.0 | 0.4 |
| 2 | 40 | 2 | 320 | 99.6 | 99.3 | 0.3 |
| 3 | 60 | 3 | 300 | 89.5 | 89.0 | 0.2 |
| 4 | 40 | 2 | 300 | 96.7 | 96.3 | 0.2 |
| 5 | 40 | 2 | 290 | 94.2 | 94.0 | 0.1 |

*acetone, diisopropyl ether, etc.

EXAMPLE 6

The procedure of Example 1 was repeated except that the catalyst was changed to γ-alumina having the following physical properties and isopropanol was fed at a flow rate of 40 ml/hr.

Gamma-alumina catalyst

Mean pore diameter: 120 Å
standard deviation ($\sigma_n$) 24 Å
Total pore volume: 0.82 cc/g
Specific surface area: 225 m²/g
Grain size: 8-14 mesh
Acidity distribution:
  pKa≦6.8: 0.22 meq/g
  pKa≦4.8: 0.04 meq/g
  pKa≦3.3: 0.02 meq/g
  pKa≦1.5: 0
Integrated acid quantity: 0.22 meq/g
Composition (dry basis):
  Na₂O: 0.17% by weight
  SiO₂: 0.06% by weight
  Fe₂O₃: 0.02 % by weight
  γ-alumina: 99.75% by weight
The results of reaction are:
Isopropanol conversion: 99.8%
Propylene yield: 99.5%

EXAMPLE 7

The procedure of Example 6 was repeated except that the reaction temperature was changed to 290° C. The results show an isopropanol conversion of 84.8% and a propylene yield of 78.8%.

COMPARATIVE EXAMPLE 1

The procedure of Example 1 was repeated except that the catalyst was changed to H-mordenite having the following physical properties and isopropanol was fed at a flow rate of 40 ml/hr through the catalyst at a temperature of 250° C.

H-mordenite catalyst

Mean pore diameter: 7 Å
Total pore volume: 0.42 cc/g
Grain size: 8-14 mesh
Acidity distribution: pKa≦−5.6: 2.07 meq/g
  Maximum acidity: pKa = −5.6
  Integrated acid quantity: 2.07 meq/g
Composition (dry basis):
  Na₂O: 0.01% by weight
  SiO₂: 97.5% by weight
  alumina: 2.5% by weight The results of reaction included an isopropanol conversion of 96.8% and a propylene yield of 70.8%. The liquid reaction mixture contained 1.4 grams of low propylene polymers in oily form. The resulting propylene contained numerous impurities including methane, ethane, and propane, and had a purity of 98.5%.

EXAMPLES 8-10

Propylene was prepared by dehydrating isopropanol by substantially the same procedure as in Example 1. Isopropanol was fed at a flow rate of 40 ml/hr. (LHVS 2 hr⁻¹) through the same catalyst as used in Example 1 at a temperature of 320° C. and a pressure as reported in Table 2. The results are shown in Table 2.

TABLE 2

| Dehydration of isopropanol under varying pressure | | |
|---|---|---|
| | Pressure (kg/cm²) | Isopropanol conversion (%) | Propylene yield (%) |
| Example 8 | 18 | 93.0 | 91.5 |
| Example 9 | 5 | 99.7 | 99.5 |
| Example 10 | atmospheric | 100 | 99.9 |

COMPARATIVE EXAMPLE 2

The procedure of Example 1 was repeated except that the catalyst was changed to γ-alumina having the following physical properties and isopropanol was fed at a flow rate of 40 ml/hr through the catalyst at a temperature of 320° C.

Gamma-alumina catalyst

Mean pore diameter: 190 Å
standard deviation ($\sigma_n$) 34 Å
Total pore volume: 0.43 cc/g
Specific surface area: 205 m²/g
Grain size: 8-14 mesh
Maximum acidity: pKa = −3.0
Integrated acid quantity: 0.14 meq/g
Composition (dry basis):
  Na₂O: 2.7% by weight
  SiO₂: 0.06% by weight
  Fe₂O₃: 0.02% by weight
  γ-alumina: 97.22% by weight The results of reaction included an isopropanol conversion of 64.1% and a propylene yield of 54.2%.

EXAMPLE 11

By following the procedure of Example 1, continuous reaction was carried out for an extended period while the amount of isopropanol fed was kept at a flow rate of 40 ml/hr. At the point of 200 hour reaction, an analysis showed an isopropanol conversion of 99.5% and a propylene yield of 99.3%. The reaction was further continued. At the point of 500 hour reaction, an analysis showed an isopropanol conversion of 99.3% and a propylene yield of 99.0%.

When the reaction time had exceeded 500 hours, the catalyst was taken out of the reactor, finding that it was somewhat grey colored. The catalyst was regenerated by heating in an electric oven at a temperature of 500° C for 3 hours. The catalyst resumed substantially the same white color as prior to use.

The catalyst was again loaded in the reactor, and dehydration of isopropanol was carried out under the same conditions as in Example 1. The results included an isopropanol conversion of 98.3% and a propylene yield of 98.0%

EXAMPLES 12-13 and COMPARATIVE EXAMPLES 3-5

A dual tube reactor was used. A reactor or inner tube of SUS 321 stainless steel having an inner diameter of 25.4 mm (1 inch) and a length of 2 m was charged with spherical γ-alumina grains having a diameter of 2 to 3 mm and the following physical properties in the amount reported in Table 3 to form a solid catalyst layer.

Gamma-alumina catalyst

Mean pore diameter: 58 Å
standard deviation ($\sigma_n$) 13 Å
Total pore volume: 0.52 cc/g
Specific surface area: 254 m²/g
Pore diameter 2-3 mm φ
Acidity distribution:
  pKa ≦ 6.8: 0.32 meq/g
  pKa ≦ 4.8: 0.10 meq/g
  pKa ≦ 3.3: 0 meq/g
  pKa ≦ 1.5: 0 meq/g
  pKa ≦ −3.0: 0 meq/g
Integrated acid quantity: 0.32 meq/g
Composition (dry basis):
  Na₂O: 0.2% by weight
  Fe₂O₃: 0.02% by weight
  SiO₂: 0.06% by weight
  γ-alumina: balance Glass beads were placed on the catalyst layer to form a gasifying layer, completing an inner tube. The inner tube was inserted into an outer tube of SUS 321 having an inner diameter of 81.1 mm and a length of 2 m. The annular space between the inner and outer tubes was filled with alumina powder as a heat medium. A porous sintered metal film was attached to the bottom of the outer tube, completing the dual tube reactor. With this dual tube reactor placed upright, nitrogen gas was blown upward from the bottom into the annular space through the sintered metal film to keep the alumina powder heat medium in a fluidized state such that a uniform temperature distribution was achieved over the entire length of the solid catalyst layer in the inner tube.

While the reactor was maintained at the temperature and pressure reported in Table 3, isopropanol was continuously fed to the reactor from its top for reaction under such conditions that the reaction factor $(M \times R \times T)/(3.6 \times P \times \pi \times r^2)$ might have the value reported in Table 3. The gas/liquid mixture exiting from the reactor bottom was separated into a liquid reaction mixture and a gas product. The liquid reaction mixture and the gas product were analyzed by gas chromatography to determine the amounts of propylene and other by-products, from which the isopropanol conversion, propylene selectivity and yield were calculated. The results are shown in Table 3.

TABLE 3

| | Comparative Example | | | | | | | | Example | | | |
|---|---|---|---|---|---|---|---|---|---|---|---|---|
| | CE3 | | CE4 | | | CE5 | | | E12 | | E13 | |
| Reaction conditions | | | | | | | | | | | | |
| Catalyst loading (ml) | 20 | | 20 | | | 100 | | | 200 | | 400 | |
| Reaction pressure (kg/cm² G) | 20 | | 10 | | | 20 | | | 18 | | 18 | |
| Isopropanol feed (ml/hr) | 60 | | 60 | | | 300 | | | 600 | | 1200 | |
| (M × R × T)/(3.6 × P × π × r²) | 0.1 | | 0.2 | | | 0.5 | | | 1.1 | | 2.1 | |
| Catalyst center temp. (°C.) | 320 | 340 | 360 | 300 | 320 | 280 | 290 | 310 | 280 | 290 | 280 | 290 |
| Results | | | | | | | | | | | | |
| Isopropanol conversion (mol %) | 80 | 96 | 99 | 81 | 99 | 59 | 88 | >99 | 73 | >99 | 71 | >99 |
| Propylene selectivity (mol %) | 87 | 96 | 99 | 70 | 95 | 84 | 95 | >99 | 90 | >99 | 88 | >99 |
| Propylene yield (mol %) | 70 | 92 | 98 | 57 | 94 | 50 | 84 | >99 | 66 | >99 | 62 | >99 |
| By-product* amount (mol %) | 13 | 4 | 1 | 30 | 5 | 16 | 5 | <1 | 10 | <1 | 12 | <1 |
| Propylene amount (mol/hr) | 0.55 | 0.72 | 0.77 | 0.45 | 0.74 | 1.95 | 3.28 | 3.85 | 5.16 | 7.69 | 9.81 | 15.39 |

*By-products include acetone, diisopropyl ether, etc.
For calculation, isopropanol (molecular weight 60) has a density of 0.785 g/cm³.

Table 4 shows combinations of the temperature and the value of reaction factor $(M \times R \times T)/(3.6 \times P \times \pi \times r^2)$ which ensure an isopropanol conversion of 99% or higher as picked up from the data of Table 3.

TABLE 4

| (M × R × T)/ (3.6 × P × π × r²) | Temperature ensuring Isopropanol conversion ≧ 99% |
|---|---|
| 0.1 | 360° C. |
| 0.2 | 320° C. |
| 0.5 | 310° C. |
| 1.1 | 290° C. |
| 2.1 | 290° C. |

As seen from Table 4, an isopropanol conversion of 99% or higher can be accomplished at a relatively low temperature of 290° C. insofar as reaction factor (M×R×T)/(3.6×P×π×r²) is higher than unity.

In commercial practice of isopropanol dehydration; it is preferred for economy and high purity of propylene to minimize the amount of unreacted isopropanol to eliminate the need to recycle the unreacted isopropanol to the reactor. This is because an extra equipment is necessary for the recycle of unreacted isopropanol and its operation adds to the cost. Since minor amounts of impurities are recycled to the reactor along with the unreacted isopropanol, such impurities build up to reduce the propylene purity. It is thus desirable from an industrial aspect to convert isopropanol into propylene at a conversion rate of at least 99%.

The fact that the temperature which ensures a maximum conversion rate of at least 99% is as low as 290° C. is advantageous in maintaining the catalyst highly active for an extended period of time while minimizing carbon deposition. Since the temperatures which ensure a maximum conversion rate of at least 99% when the reaction factor (M×R×T)/(3.6×P×π×r²) has values of 0.5 and 1.1 are 310° C. and 290° C., catalyst life tests were carried out for about 1,500 hours at the temperatures of 310° C. (under the conditions of Comparative Example 5) and 290° C. (under the conditions of Example 12). A substantial loss of activity as demonstrated by a conversion reduction from 99% to 90% was observed in the former case while only a slight loss of activity was observed in the latter case as demonstrated by a conversion reduction from 99% to 97%. At the end of the catalyst life tests, the catalysts were taken out of the reactors, finding that the amount of carbon deposited on the catalyst was 13% for the former case, but 3% for the latter case.

According to the process of the present invention, propylene can be prepared from isopropanol in higher yields with higher selectivity than in the prior art. It becomes possible to provide for utilization of acetone which is a by-product in preparing phenol by the cumene process, by converting the acetone into isopropanol and then converting the isopropanol into propylene in high yield and selectivity according to the present invention. The resulting propylene is useful as the starting reactant for preparing various organic compounds and polyolefins. The present invention is of great industrial value.

Although some preferred embodiments have been described, many modifications and variations may be made thereto in the light of the above teachings. It is therefore to be understood that within the scope of the appended claims, the invention may be practiced otherwise than as specifically described.

We claim:

1. A process for preparing propylene comprising the step of dehydrating isopropanol at about 180° C. to about 400° C. in the presence of an γ-alumina catalyst having a mean pore diameter in the range of from 30 to 150 Å with a standard deviation ($\sigma_n$) in the range of from 10 to 40 Å and a pore volume of at least 0.4 cc/g, on a dry basis, based on statistic calculation from pore diameter and pore volume, wherein said γ-alumina catalyst is prepared from pseudo-boehmite aluminum hydroxide through dehydration.

2. The process of claim 1 wherein said γ-alumina is used in the form of a catalyst layer and isopropanol in a gaseous state is passed through the catalyst layer in a direction so as to satisfy the following equation:

$$(M \times R \times T)/(3.6 \times p \times \pi \times r^2) \geq 1 \qquad (I)$$

wherein
M is moles of isopropanol fed per hour, mol/hr,
R is the gas constant equal to 0.082 l·atm/deg·mol,
T is the temperature of the catalyst layer in °K.,
P is the reaction pressure in atm,
π is the circle ratio equal to 3.14, and
r is a radius of the catalyst layer in a cross section transverse to the direction of flow of isopropanol in cm.

3. The process of claim 1 wherein said γ-alumina catalyst is a low alkali content γ-alumina comprising at least 90% by weight of γ-alumina, less than 10% by weight of silica, and up to 0.5% by weight of an alkali metal oxide.

4. The process of claim 1 wherein said γ-alumina catalyst is a weakly acidic γ-alumina having a pKa value in the range of from +3.3 to +6.8 as measured with Hammett's indicator and as integrated acid quantity of up to 0.5 meq/g on dry basis.

5. The process of claim 1 wherein said γ-alumina catalyst has a mean pore diameter in the range of from 40 to 70 Å with a standard deviation ($\sigma_n$) in the range of from 10 to 20 Å.

6. The process of claim 1 wherein said γ-alumina catalyst has a total pre volume of 0.05 to 0.8 cc/g on a dry basis.

* * * * *